United States Patent [19]

Wiesner et al.

[11] 4,259,240
[45] Mar. 31, 1981

[54] SYNTHESIS OF FURYL INTERMEDIATES, AND CARDENOLIDES AND THEIR ISOMERS PREPARED THEREFROM

[75] Inventors: Karel Wiesner; Thomas Y. R. Tsai, both of Fredericton, Canada

[73] Assignee: Advance Biofactures Corporation, Lynbrook, N.Y.

[21] Appl. No.: 80,004

[22] Filed: Sep. 28, 1979

[51] Int. Cl.$^3$ .............................................. C07J 71/00
[52] U.S. Cl. ........................ 260/239.55 R; 260/239.57
[58] Field of Search ....................... 260/239.55, 239.57

[56] References Cited

U.S. PATENT DOCUMENTS 4,102,884  7/1978  Kruger ........................... 260/239.57
4,150,127  4/1979  Anner et al. .................... 260/239.57

*Primary Examiner*—Elbert L. Roberts
*Attorney, Agent, or Firm*—Roland Plottel

[57] ABSTRACT

The invention relates to furyl intermediates and the preparation thereof, said intermediates being particularly useful in the preparation of synthetic cardenolides and their isomers. The process provides for the reaction of an unsaturated steroidal 17 ketone with a β-furyl compound to produce an allylic alcohol which is subjected to acetylation and allylic rearrangement. The resulting material is then hydrogenated to produce the furyl intermediate. Cardenolides are formed therefrom by oxidation of the furyl intermediates.

18 Claims, No Drawings

SYNTHESIS OF FURYL INTERMEDIATES, AND CARDENOLIDES AND THEIR ISOMERS PREPARED THEREFROM

This invention relates to the preparation of certain furyl intermediates and to the synthesis of synthetic cardenolides and their isomers from said intermediates.

BACKGROUND OF THE INVENTION

Cardenolides are aromatic compounds that can be and are used to treat people suffering from various heart diseases. These materials include digitalis which is a mixture of glycosides and affords on hydrolysis a mixture of the aglycones, for example, digitoxigenin, digoxigenin, gitoxigenin, and many others which are also cardenolides. These substances conform in skeletal structure; with the exception of the placement of hydroxyl groups they all have twenty-three carbon atoms present and are of the cis-decalin type. They are all sterols and are characterized structurally by the presence of a saturated phenanthrene ring system having an additional five membered ring fused thereto. The distinguishing structural features of the cardenolides are the $\beta$-oriented hydroxyl group at $C_{14}$ and as stated the five-membered $\alpha,\beta$-unsaturated lactone ring. As indicated above, the compounds are of the cis-decalin type, the angular methyl group and side chain are $\beta$ oriented, the B/C ring structure is trans while the C/D structure is cis since $C_{14}$ has the $\beta$ configuration. This is structurally shown in Formula I.

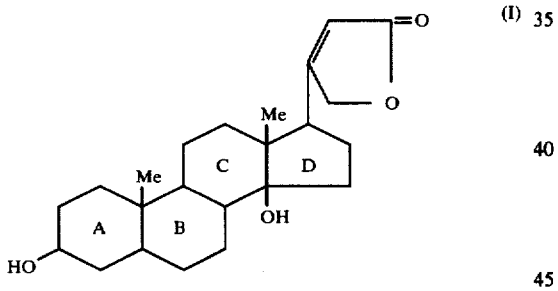

which represents digitoxigenin. Digoxigenin and gitoxigenin have an additional hydroxyl group on the 12-carbon and 16-carbon respectively.

Furyl derivatives of cardenolides have been heretofore obtained by hydride reduction of naturally occurring cardenolides. These derivatives obtained from naturally occurring cardenolides have the structure shown in Formula II.

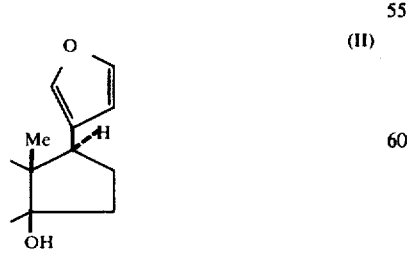

Oxidation of these furyl derivatives with peracids or N bromo succinimide respectively yielded selectively lactones of the types III and IV.

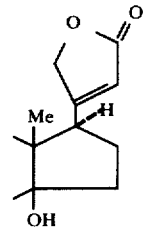

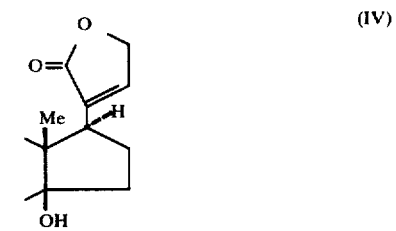

(J. M. Ferland, Y. Lefebre, R. Deghenghi and K. Wiesner, Tetrahedron Letters, No. 30, 3617 (1966).)

SUMMARY OF THE INVENTION

It is the primary object of the subject invention to provide a synthesis of furyl intermediates useful in the subsequent production of synthetic cardenolides and their isomers.

A second object of the instant invention is to use said furyl intermediates to produce said synthetic cardenolides and their isomers.

Another object of the invention is to provide a total synthesis for digitoxigenin and its isomer.

Still other objects will become apparent from the ensuing description and claims.

Furyl derivatives of the invention have the structure shown in Formula V.

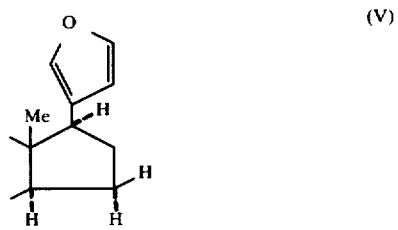

An illustrative furyl intermediate is shown by Formula VI.

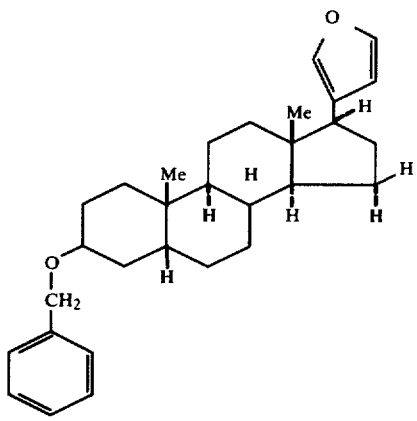

(VI)

According to this invention, a synthesis of such intermediate comprises the step of treating a suitable 17 position steroidal ketone shown below in VII

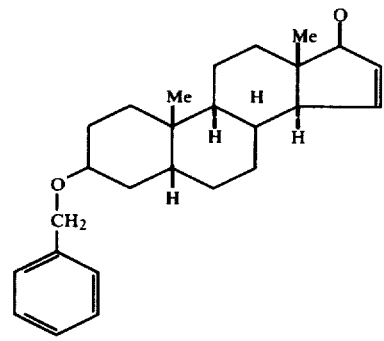

(VII)

with an alkali or alkaline earth metal β-furyl compound, e.g., β-furyl lithium to form the tertiary carbinol of Formula VIII set forth below:

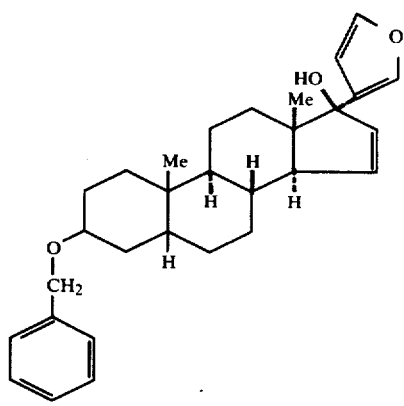

(VIII)

This allylic alcohol is then subjected to acetylation and a stereospecific allylic rearrangement resulting in the compound shown by Formula IX below:

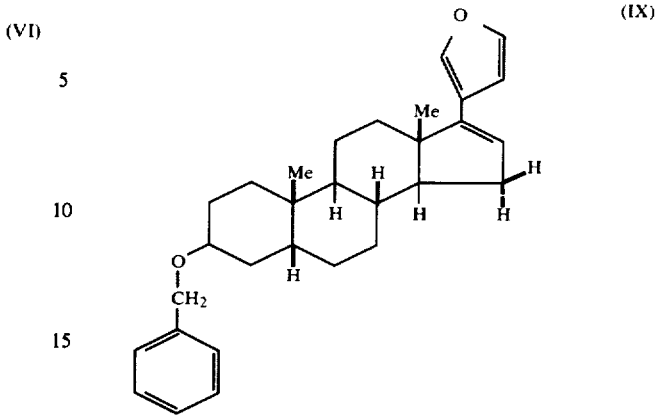

(IX)

This compound (IX) is then hydrogenated to form the furyl intermediate. In this manner furane is inserted stereospecifically into the configuration, which it must have in order to be convertible into cardiotonic material. At the same time the $C_{15}\beta$ hydroxyl provides a route for changing the CD trans into the required CD cis configuration and for the introduction of the $C_{14}\beta$ hydroxy group necessary in the cardenolides.

DETAILED DESCRIPTION OF THE INVENTION

The 17-steroidal ketones are known in the art and can be readily prepared from testosterone or other well known steroids (McQuillen et. al., Journal of Chemical Society, pg. 5996 (1963); (Danielsson et. al., Journal Biog. Chem. 237, 3657 (1962); Kelly et. al., Journal Chemical Society, pg. 416 (1969)).

The following description illustrates an 11 step manner of preparation of the steroidal ketone useful in the preparation of the furyl intermediates:

(1) Commercial testosterone (25 g.) was dissolved in ethanol (400 ml.) and dioxane (100 ml.). Potassium hydroxide solution (1.5 g. in 20 ml. of water) was added to bring the pH of the solution to 10.5. 10% Palladium on calcium carbonate (3 g.) was added and the suspension was hydrogenated at atmospheric pressure until there was no more uptake of hydrogen. The catalyst was filtered off through a Celite pad and the solvent was evaporated in vacuo to give a yellowish gum. The product alcohol crystallized out on addition of ice water, and was recrystallized from acetone-hexane. The yield was 24.1 g. (96.4%, m.p. 137°-140° C.).

(2) The alcohol (24 g., 82 mol) was dissolved in dry methylene chloride (500 ml.). Dihydropyran (14 g.) was added followed by pyridinium p-toluenesulphonate (2.5 g.). After 4 hours the solution was evaporated to a small volume and then diluted with ether (1 L). The ether solution was washed with brine, dried over magnesium sulfate and evaporated to afford the product ketone as a gum which crystallized on trituration with hexane at 0° C. (30.1 g., 96.3%, m.p. 83°-5° C.).

(3) The ketone thus formed (30 g.) was dissolved in absolute benzene (150 ml.) and sec-butyl alcohol (450 ml.) was added. Aluminum t-butylate (80% in t-butyl alcohol, 35 g.) was then added and the suspension was heated under reflux for 15 minutes. The reaction mixture was then added to ice-water and the resulting solid extracted with 1:3 methylene chloride-ether (3×500 ml.). The combined organic extracts were washed with saturated ammonium chloride and brine, dried over sodium sulfate, and evaporated to afford the mixture of compounds 4a and 4b. The mixture was separated by short-column chromatography with ether-hexane 3:7 as solvent to give two compounds one having a melting point of 148°–150° C. and another having a melting point of 129°–130° C., in a total yield of 94.5%.

(4) 19 grams of the second compound in dry methylene chloride was added while vigorously stirring to a suspension of chromium trioxide pyridine complex. Stirring was continued until the reaction was completed (20 min.). The solvent was decanted and the complex washed with more methylene chloride (2×200 ml.). The solvent was then reduced to a small volume in vacuo and diluted with ether (800 ml.). The ethereal layer was washed with saturated sodium bicarbonate, followed by brine. The total organic extract was dried over magnesium sulfate and evaporated to yield the ketone from the previous step as a gum (18 g.). This material was used directly without purification and reduced to the mixture of the two compounds above.

(5) The first compound (1.03 g.) was dissolved in dry dioxane (50 ml.) and sodium hydride (360 mg., 57% dispersion in oil) was added under an atmosphere of nitrogen. The suspension was heated with stirring under reflux for 4 hours and then allowed to cool. Benzyl bromide (560 mg.) was added and refluxing was continued for a further 2 hours. The suspension was filtered through a sintered glass funnel and the filtrate was evaporated in vacuo to give the product as a gum. This material was used directly for the next reaction without purification (1.1 g.).

(6) The crude product from (5) above (1.1 g.) was dissolved in 2% hydrochloric acid in methanol (150 mg.) and stirred for 1 hr. The solution was neutralized with 10% sodium hydroxide and the volume of methanol reduced in vacuo. The aqueous residue was then extracted with 1:3 methylene chloride-ether (3×100 ml.). The combined organic extracts were washed with brine, dried over sodium sulfate and evaporated to afford a product alcohol as a form (900 mg.)

(7) The alcohol (13 g.) was dissolved in dry methylene chloride (200 ml.) and added to a rapidly stirring suspension of the chromium trioxide pyridine complex (50 g.) in dry methylene chloride (800 ml.) at room temperature. Stirring was continued for further 20 min. and the solvent decanted and evaporated in vacuo to a small volume. Ether (600 ml.) was added and the organic layer washed with saturated sodium bicarbonate followed by brine. Drying, evaporation of the solvent and crystallization from ethanol yielded a ketone (11.3 g., 87.9%, m.p. 134°–6° C.).

(8) The ketone (11 g.) was dissolved in absolute benzene (350 ml.) and ethylene glycol (25 ml.) and p-toluenesulphonic acid (1.1 g.) were added. The solution was heated, with stirring, under reflux for 5 hr. and water was collected by means of a Dean-Stark apparatus. The solution was then allowed to cool and it was diluted with more benzene (50 ml.), and washed with saturated sodium bicarbonate, followed by brine. Drying, evaporation of the benzene and crystallization from ether-hexane gave the product, m.p. 95°–7° C. (97%).

(9) The acetal (12 g.) thus formed was dissolved in freshly distilled tetrahydrofuran (30 ml.). Pyridinium bromide perbromide (10 g.) was dissolved in dry tetrahydrofuran (30 ml.) and added to the solution under a nitrogen atmosphere. The solution was stirred for 1 hr. after which time there was precipitation and lightening of the colour of the reaction mixture. Sodium iodide (7.5 g.) was added to the suspension and stirring was continued for a further 15 min. The solution was then diluted with ether and washed with saturated sodium thiosulfate followed by brine. Drying and evaporation yielded a product bromoacetal as a gum which was crystallized from aqueous methanol (11.5 g., 80.9%, m.p. 109°–111° C.).

(10) The bromoacetal (11.5 g., 23 mmol) was partially dissolved in dimethylsulfoxide (150 ml.) and potassium t-butoxide (12 g., 98 mmol) was added under a nitrogen atmosphere. The suspension was stirred at 40° C. for 12 hr. and the resulting solution was poured into dry ether (1 liter). The ether was then washed with water, followed by brine. The ether solution was dried over magnesium sulfate and evaporated to dryness to afford the product acetal as a foam (8.8 g., 90%).

(11) This acetal (8.8 g.) was dissolved in acetone (300 ml.) and p-toluenesulphonic acid (1 g.) was added followed by water (40 ml.). The solution was stirred for 3 hr. at room temperature and diluted with 3:1 ether-methylene chloride (1 liter). The solution was then washed with saturated sodium bicarbonate and by brine. Drying and evaporation of the solvent afforded the steroidal ketone as a white solid which was recrystallized from ether-hexane (m.p. 151°–3° C., 7.5 g., 95%).

Thus the product useful as the starting material for the preparation of a furyl intermediate is an α,β-unsaturated ketone having steroidal properties.

As stated, the furyl intermediate of the subject invention then can be prepared by treating the above ketone compound with β-furyl lithium in ether. In addition to diethyl ether, other ethers can be employed such as for example, dioxane and tetrahydrofuran. This produces the tertiary carbinol or allylic alcohol of Formula VIII above. As stated this material is then acetylated. This can be done by reacting said alcohol with acetic anhydride and pyridine. The crude acetate can then be subjected to an allylic rearrangement by refluxing in aqueous acetone in the presence of calcium carbonate. The resulting secondary allylic alcohol of Formula IX above is obtained after chromatography on silica gel. It should be pointed out that the rearrangement is stereospecific and yields the 15-β hydroxy compound in spite of the clear preference of the system for a nucleophillic attack from the α-side. Hydrogenation of the secondary allylic alcohol with 10% Pd-CaCO₃ in ethanol was stereospecific and gave the saturated furyl derivative (m.p. 109°–110° C.).

In synthesizing the furyl derivatives from the starting ketone, advantage is made of the stereospecific properties thereof. As with other CD-trans-steroids, this compound is attacked by nucleophiles from the alpha side. Thus, if one treats the ketone with β-furyl lithium the allylic alcohol such as shown in Formula VIII is obtained.

This allylic alcohol VIII has the hydroxy group in the beta configuration and the furyl group in the alpha configuration. If one subjects this allylic alcohol to acetylation, an allylic rearrangement occurs. This rearrangement is stereospecific and the hydroxyl group in Formula IX is beta. This secondary allylic alcohol still has CD-trans-fusion and consequently, it is still attacked by reagents from the alpha side. If one now hydrogenates, the hydrogen comes from the alpha side and thus the furan ends up in the bath configuration as shown in Formula VI. It is in this manner that the furane is stereospecifically placed in this configuration required in cardiotonic compounds.

The presence of the 15β-hydroxy group in the furyl intermediate is necessary since it enables the conversion of the substance into an actual cardenolide. The synthesis of a furyl intermediate without the $C_{15}\beta OH$ would be useless since it would be a dead end; the conversion of CD trans into CD cis and insertion of the $C_{14}\beta OH$ would be impossible. These are essential features of cardenolides. In the process of this invention, it should be noted that temperature is not critical; however, it has been found that yields are better and produces less contaminated by impurities if temperatures are kept low, on the order of 0° to −80° C. in the first step of Example I.

A more detailed synthesis of the furyl derivatives is given in the following Examples:

EXAMPLE I n-Butyl lithium (5.3 ml., 2.2 M solution) was added to a stirred solution of 3-bromofuran (1.87 g.) in absolute ether (30 ml.) at −70° C. and the mixture was stirred for 1 hr. An ether solution (40 ml.) of the α,β-unsaturated ketone of Formula VII (2 g.) was then added dropwise and the solution was stirred for 30 min. at the same temperature. Excess reagent was destroyed by slow addition of water and the mixture was washed with 5% citric acid, 5% $NaHCO_3$, dried over anhydrous $MgSo_4$ and evaporated to dryness to yield 2.2 g. of the allylic alcohol of Formula VIII (93%) which was used for the next step without further purification.

M/e=446.

I.R. $(CHCl_3)\nu max$: 3600 cm$^{-1}$ (OH).

N.M.R. $(CDCl_3)$ τ: 2.65 (s, 5H, benzyl aromatic), 2.57, 2.78, 3.58 (broad s, 1H each, furyl), 3.91 (d, J=6, 1H, 15-H), 4.28 (dd, J=6, 1H, 16-H), 5.52 (s, 2H, benzylic), 6.3 (broad s, 1H, 3αH), 9.0 (s, 3H, 18-CH$_3$), 8.96 (s, 3H, 19—CH$_3$).

The allylic alcohol of Formula VIII (4.46 g.) was acetylated with acetic anhydride (5 ml.) in pyridine (10 ml.) in the presence of a catalytic amount of 4-dimethylaminopyridine (11 mg.) at room temperature for 12 hr. The reaction mixture was evaporated at 50° C. in vacuo to dryness and the residue was redissolved in ether, washed with 5% citric acid, 5% $NaHCO_3$, dried and evaporated to dryness in vacuo to give quantitatively the acetate which was used for the rearrangement without further purification.

M/e=488.

I.R. $(CHCl_3)_{\nu max}$: 1728 cm$^{-1}$ (>C=O).

N.M.R. $(CDCl_3)$ τ: 2.61 (s, 6H, benzyl aromatic and furyl, 2.41, 3.44 (broad s, 1H each, furyl), 7.96 (s, 3H, acetoxy methyl), 8.72 (s, 3H, 18—CH$_3$), 8.92 (s, 3H, 19—CH$_3$).

The crude acetate (4.65 g.) was refluxed in aqueous acetone (200 ml., 25% H$_2$O) in the presence of CaCO$_3$ (2. g.) for 24 hr. The filtrate of the reaction mixture was seprated under reduced pressure to remove most of the acetone and the crude product was dissolved in ether, washed with 5% NaHCO$_3$, dried over anhydrous MgSO$_4$ and evaporated to dryness. The product was purified by column chromtography on silica gel and yielded the pure secondary allylic alcohol (3.8 g., 87% in two steps).

M/e=446.

I.R. (CHCl$_3$) $\nu_{max}$:3605 cm$^{-1}$ (OH), no acetoxy carbonyl absorption.

N.M.R. (CDCl$_3$) τ: 2.67 (s, 6H, benzyl aromatic and furyl), 2.48, 3.5 (broad s, 1H each, furyl), 4.08 (d, J=3, vinylic H), 5.47 (broad s, 1H, 15α-H), 5.51 (s, 2H, benzylic), 6.28 (broad s, 1H, 3α-H), 8.71 (s, 3H, 18—CH$_3$), 8.93 (s, 3H, 19—CH$_3$).

The secondary allylic alcohol (3.57 g.) was hydrogenated in ethanol with 10% Pd/CaCO$_3$ (357 mg.) at room temperature. The catalyst was removed by filtration through Celite and the filtrate was evaporated in vacuo to yield the product furyl derivative which was crystallized from ether-hexane and melted at 109°-110° C. (3.3 g., 92%).

M/e=448.

I.R. (CHCl$_3$) $\nu_{max}$:3605, 3420 cm$^{-1}$ (OH).

N.M.R. (CDCl$_3$) τ: 2.63 (s, 6H, benzyl aromatic and furyl), 2.75, 3.68 (broad s, 1H each, furyl), 2.75, 3.68 (broad s, 1H each, furyl), 5.49 (s, 2H, benzylic), 5.65 (t, J=7, 1H, 15α-H), 6.28 (broad s, 1H, 3α-H), 8.97 (s, 3H, 19—CH$_3$), 9.21 (s, 3H, 18—CH$_3$).

The product furyl derivative produced in accordance with the above teachings is useful to produce cardenolides and their isomers. The first step in such production is the oxidation of the furyl derivative by a peracid to ultimately obtain a normal cardenolide or by a material such as N-bromosuccinimide or the like to ultimately form the cardenolide isomers.

The oxidation of the group is structurally shown below where A represents the starting furan. The oxidation

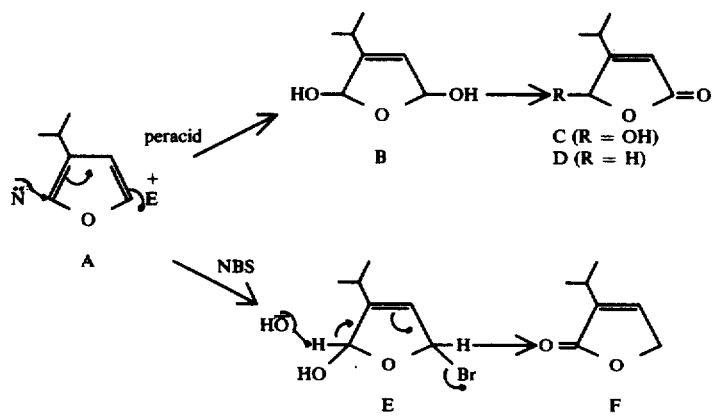

may be represented as an attack of an electrophile at the lesshindered alpha position followed by a nucleophilic attack at the remaining alpha-site.

Peracid oxidation is believed to proceed via the intermediate B which undergoes further oxidation to the hydroxylactonec. This last compound can be readily reduced with NaBH₄ to the unsaturated lactone D. In the case of N-bromo-succinimide, it leads to the intermediate E which yields the lactone F by elimination of HBr. The yields of these reactions show considerarble improvement other yields achieved when the furyl derivatives are obtained, as in the past, by the hydride reduction of natural cardenolides.

The following illustrates a manner in which this can be done:

The furyl derivative is treated with m-chloroperbenzoic acid in a mixture of chloroform, acetic acid and sodium acetate.

The crude oxidation product, which contains mostly the corresponding hydroxylactone, is immediately, without isolation, reduced in a two phase-system ($CH_2Cl_2$—$H_2O$) at room temperature with sodium borohydride for three hours. The pure oily lactone product is obtained after chromatography on silica gel in a yield of about 87%. Treatment of the lactone with mesyl chloride in pyridine yields about 85% of the crystalline unsaturated product of Formula X (m.p. 151°-2° C.). The elimination of the 15β

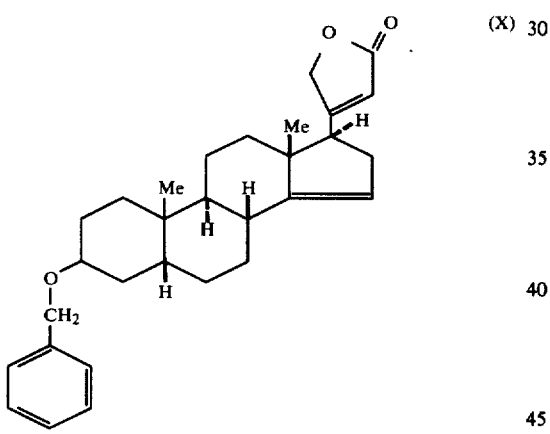

(X)

hydroxyl which yields specifically the 14-15 unsaturated compound is an important part of the invention. The formation of the double bond would not be possible if the $C_{15} \beta$ hydroxyl was absent, The introduction of the 14-hydroxyl function is performed by a modification of the method described by Engel and Bach in Steroids, Volume 3, page 593 (1964). The olefin is brominated with N-bromoacetamide in an acetic acid-water-acetone mixture and the crude reaction product is stirred with Ra-Ni in a mixture of methylene chloride, methanol and potassium acetate. Under these conditions the reaction is regio- and stereo-specific and gives 3-benzyl digitoxigenine (m.p. 152°-3° C.) in a yield of about 78% after cyrstallization from ether-chloroform. Finally, hydrogenolysis of the benzyl group over Pd-charcoal in an ethanolbenzene mixture yields about 93% of crystalline (m.p. 253°-255° C.) digitoxigenine which was identical with the natural compound by mixed melting point, thin layer chromatography (T.L.C.) and all spectral data.

In order to synthesize the digitoxigenine isomer the furan intermediate can be oxidized with N-bromosuccinimide in a mixture of sodium acetate, water and dioxane. The crude oxidation product is treated with zinc in acetic acid to produce the small amount of brominated material. The pure oily lactone is isolated by chromatography on silica gel in a yield of about 83%. The conversion of this 15β-hydroxy lactone to the desired final product isomer is performed in exactly the same manner as the transformation of the oily isomeric lactone above to digitoxigenine.

Dehydration of the oily lactone yields about 87% of a crystalline lactone of Formula XI (m.p. 159°-161° C.)

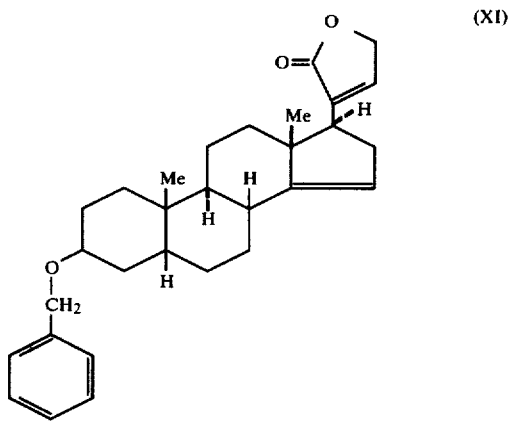

(XI)

Hydroxylation of this material gives about 75% of the benzyl hydroxy lactone of Formula XII (m.p. 130°-1° C.).

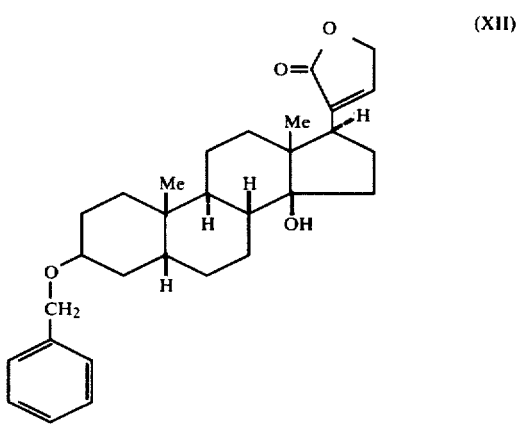

(XII)

Finally, hydrogenolysis of this last derivative gives the totally synthetic digitoxigenine isomer of Formula XIII (m.p. 101°-3° C.) in a yield of about 90%.

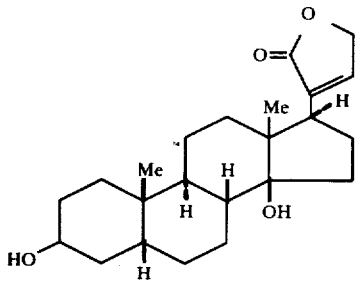

(XIII)

This isomer is identical in all respects with the same material prepared from natural digitoxigenine. It is believed that the simple synthetic operations disclosed herein will form an efficient basis for a systematic manipulation of the cardenolide molecule with the objective of achieving a further improvement in its therapeutic parameters.

Thus as indicated above, once the furyl derivative is obtained, the furane is changed to the desired lactone. As shown this is done by oxidation using any peracid for the normal cardiotonic compound or N-bromo-succinimide in order to get the isomer. In the case of the isomer, any reagent which generates a bromonium ion will suffice.

Therefore, one capitalizes on the favorable reactivity of the CD-trans-ring system and is then able to change the trans to the cis form. The naturally occuring cardenolides are cisoid.

The final step is to change the trans to the cis form. By means of the process of this invention, by the use of suitable substituents, a wide variety of desired cardenolides can be prepared. The hydroxyl group has been moved to the 14β-position by the final steps.

The following examples specifically illustrate the formation of digitoxigenine and its isomer:

EXAMPLE 2

A mixture of the furyl derivative of Formula VI (134.4 mg.), sodium acetate (61.5 mg.) and acetic acid (45 mg.) in chloroform (6 ml.) was treated with m-chloroperbenzoic acid (114 mg.) and stirred at room temperature for 2 hr. Chloroform (10 ml.) was then added and the mixture was washed with 5% $Na_2SO_3$, 5% $NaHCO_3$, dried over anhydrous $MgSO_4$ and evaporated to dryness. The crude hydroxylactone thus obtained was reduced with $NaBH_4$ (57 mg.) in a $CH_2Cl_2$—$H_2O$ mixture (30 ml. $CH_2Cl_2$, 6 ml. $H_2O$) at room temperature for 3 hr. The mixture was then acidified with 5% citric acid, extracted with ether, the ether extract dried over anhydrous sodium sulfate, and evaporated to dryness. The material was purified by preparative TLC yielding 97.5 mg. (87%) of the pure oily 15β hydroxy lactone.

M/e=464.

I.R. $(CHCl_3)_{vmax}$: 3610, 3480 (OH), 1785, 1750 cm$^{-1}$ (>C=O).

N.M.R. $(CDCl_3)\tau$: 2.64 (s, 5H, benzyl aromatic), 4.11 (broad s, 1H, 22—H), 5.23 (broad s, 2H, 21—H), 5.48 (s, 2H, benzylic), 5.62 (t, J=7, 1H, 15α-H), 6.27 (broad s, 1H, 3α—H), 8.97 (s, 3H, 19—$CH_3$), 9.09 (s, 3H, 18—$CH_3$).

The 15β hydroxy lactone (185.6 mg.) in pyridine (2 ml.) was stirred with mesyl chloride (55 mg.) at 60° C. for 4 hr. followed by evaporation in vacuo to dryness. The residue was dissolved in ether and washed with 5% citric acid, 5% $NaHCO_3$, dried over anhydrous $MgSO_4$ and evaporated to dryness. The crude material was purified by preparative TLC to yield the pure unsaturated lactone (X) (152 mg., 85%) which was crystallized from ether-hexane, m.p. 151°-2° C.

M/e=446.

I.R. $(CHCl_3)_{vmax}$: no hydroxy absorption, 1784, 1750 cm$^{-1}$ (>C=O).

N.M.R. $(CDCl_3)\tau$:2.67 (s, 5H, benzyl aromatic), 4.11 (t, J=1, 1H, 22-H), 4.77 (d, J=2, 1H, 15-vinylic), 5.25 (d, J=2, 2H, 21—H), 5.49 (s, 2H, benzylic), 6.28 (broad s, 1H, 3β-H), 9.01 (s, 3H, 19—$CH_3$), 9.18 (s, 3H, 18—$CH_3$).

A mixture of the pure lactone (89.5 mg.), acetic acid (18 mg.) and water (0.3 ml) in acetone (3 ml.) was stirred with N-bromo-acetamide (34.5 mg.) at room temperture for 30 min. The reaction mixture was diluted with $CH_2Cl_2$, washed with 5% $Na_2SO_3$, dried over anhydrous $MgSO_4$ and evaporated at room temperature in vacuo to dryness. The residue was redissolved in a 1:1 mixture of $CH_2Cl_2$ and MeOH (4 ml.) and stirred at room temperature with Ra-Ni (3 g.) in the presence of potassium acetate (30 mg.) for 1 hr. Ra-Ni was filtered off and the filtrate was washed with water, dried over anhydrous $MgSO_4$ and evaporated to dryness. The crude product was purified by preparative TLC and yielded the pure benzyl digitoxigenine (84 mg., 78%) after crystallization from ether-$CHCl_3$ (m.p. 152°-3° C.).

M/e=464.

I.R. $(CHCl_3)$ $vmax$: 3600, 3450 (OH), 1785, 1748 cm$^{-1}$ (>C=O) N.M.R. $(CDCl_3)\tau$: 2.65 (5, 5H, benzyl aromatic), 4.13 (t, J=2, 1H, 22-H), 5.12 (t, J=2, 2H, 21—H), 5.5 (s, 2H, benzylic), 6.28 (broad s, 1H, 3α-H), 9.03 (s, 3H, 19—$CH_3$), 9.11 (s, 3H, 18—$CH_3$).

The benzylidigitoxigenine (93 mg.) was dissolved in an ethanol-benzene mixture (16 ml. ethanol, 4 ml. benzene) and hydrogenated over 10% Pd/C (18.6 mg.) at atmospheric pressure and room temperature for 3 hr. followed by filtration through Celite. The filtrate was evaporated under reduced pressure yielding synthetic digitoxigenine (70 mg., 93%) which was crystallized from ether-chloroform, m.p. 253°-255° C.

The synthetic digitoxigenine was identical with natural digitoxigenine in all spectral data, TLC and also gave no melting point depression.

M/e=374.

I.R. $(CHCL_3)_{vmax}$: 3610, 3455 (OH), 1783, 1748 cm$^{-1}$ (>C=O).

N.M.R. $(CDCl_3)\tau$:4.11 (t, J=2, 1H, 22-H), 5.08 (t, J=2, 2H, 21-H), 5.85 (broad, s, 1H, 3α-H), 9.01 (s, 3H, 19—$CH_3$), 9.1 (s, 3H, 18—$CH_3$).

EXAMPLE 3

A mixture of the furyl derivative (VI) (179.2 mg.), sodium acetate (56 mg.) water (0.4 ml.) and dioxane (8 ml.) was treated with N-bromosuccinimide (a total of 121 mg.) in small portions at room temperature until the color no longer discharged in 10 min. The mixture was then diluted with ether (20 ml.) and washed with 5% $Na_2SO_3$, 5% $NaHCO_3$, dried and evaporated to dryness. The residue was dissolved in acetic acid (3 ml.) and stirred with zinc (1.5 g., 30 mesh) at room temperature for 30 min. The crude product obtained after work up in the usual manner was purified by preparative TLC to give the pure oily 15β hydroxy lactone (155 mg., 83%).

M/e=464.

I.R. (CHCl₃)$\nu_{max}$: 3610, 3470 (OH), 1752 cm$^{-1}$ (>C=O).

N.M.R. (CDCl₃)τ:2.69 (s, 5H, benzyl aromatic), 2.86 (broad s, 1H, 22-H), 5.25 (broad s, 2H, 23-H), 5.53 (s, 2H, benzylic), 5.72 (t, J=7, 1H, 15α-H), 6.28 (broad s, 1H, 3α-H), 9.0 (s, 3H, 19—CH₃), 9.17 (s, 3H, 18—CH₃).

The 15β hydroxy lactone (139.5 mg.) in pyridine (2 ml.) was treated with mesyl chloride (42 mg.) at room temperature followed by stirring at 60° C. for 4 hr. The reaction mixture was worked up in the manner already described in the preparation of the crytalline lactone of Example 2 above. The crude product obtained was purified by preparative TLC to yield the pure crystalline unsaturated lactone (116 mg., 87%) which was crystallized from ether-hexane, m.p. 159°-160° C.

M/e=446.

I.R. (CHCl₃)$\nu_{max}$: no hydroxy absorption, 1755 cm$^{-1}$ (>C=O).

N.M.R. (CDCl₃)τ:2.65 (s, 5H, benzyl aromatic), 2.81 (t, J=2, 1H, 22-H), 4.76 (d, J=2, 1H, 15-vinylic), 5.2 (t, J=2, 2H, 23-H), 5.5 (s, 2H, benzylic), 6.26 (broad s, 1H, 3α-H), 9.01 (s, 3H, 19—CH₃), 9.23 (s, 3H, 18—CH₃).

The crystalline lactone (134 mg.) in acidified aqueous acetone (27 mg. acetic acid, 4.5 ml. acetone, 0.45 ml. H₂O) was stirred with N-bromoacetamide (52 mg.) at room temperature for 30 min. The reaction mixture was diluted with CH₂CL₂, washed with 5% Na₂SO₃, dried over anhydrous MgSO₄ and evaporated at room temperature to dryness. The residue was redissolved in a 1:1 mixture of CH₂Cl₂ and MeOH (4 ml.) and stirred at room temperature with Ra-Ni. Preparative TLC yielded the pure isolactone (105.5 mg., 75%) (m.p. 212°-3° C.)

I.R. (CHCl₃)$\nu_{max}$: 3600, 3440 cm$^{-1}$ (OH), 1750 cm$^{-1}$ (>C=O).

N.M.R. (CDCl₃) τ: 2.67 (s, 6H, benzyl aromatic and 22-H), 5.23 (d, J=2, 2H, 23—H), 5.51 (s, 2H, benzylic), 6.28 (broad s, 1H, 3α-H), 9.03 (s, 3H, 19—CH₃), 9.16 (s, 3H, 18—CH₃).

The hydroxy isolactone (70 mg.) was hydrogenated exactly as described for the hydrogenolysis of the benzyldigitoxigenine and yielded the digitoxigenine isomer (50 mg., 90%) which was crystallized from ether-chloroform and melted at 101°-3° C. The synthetic compound was identical in all respects with the previously described material of the same structure.

M/e=374.

I.R. (CHCl₃) $\nu_{max}$: 3610, 3445 (OH), 1747 cm$^{-1}$ (>C=O).

N.M.R. (CDCl₃) τ: 2.67 (broad s, 1H, 22—H), 5.17 (d, J=2, 2H, 23—H), 5.83 (broad s, 1H, 3α-H), 9.03 (s, 3H, 19—CH₃), 9.16 (s, 3H, 18—CH₃).

The foregoing examples and discussion describe the syntheses which are the subject of the instant invention. It is possible, within the scope of the present invention to use various other reagents to perform the same chemical processes.

BEST MODE CONTEMPLATED

The best mode contemplated for carrying out this invention has been set forth in the description above, for example, by way of setting forth preferred structural arrangements, materials used, compositions and operating conditions, including but not limited to preferred ranges and values of amounts, temperatures, pressures, and other unobvious variable materials to successfully practicing (including making and using) the invention in the best way contemplated at the time of executing this patent application.

It is understood that the foregoing detailed description is given merely by way of illustration and that many modifications may be made therein without departing from the spirit or scope of the present invention.

What is claimed is:

1. A process for the preparation of a 17 β-furyl, 15 β-hydroxyl intermediate suitable for the total synthesis of cardenolides or their isomers which comprises the steps of:
   (a) reacting an α,β unsaturated steroidal 17 ketone with an alkali or alkaline earth metal β-furyl compound to form a CD-trans-oid allylic alcohol;
   (b) acetylating said alcohol and subjecting the resulting acetate to a stereospecific allylic rearrangement to produce a CD-trans-oid 15 β-hydroxyl compound;
   (c) hydrogenating said 15 β-hydroxyl compound to form the 17 β-furyl, 15 β-hydroxyl intermediate.

2. The process as claimed in claim 1 wherein said α,β unsaturated steroidal ketone has the structure

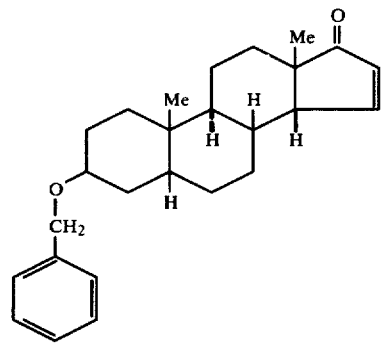

3. The process as claimed in claim 1 wherein said β-furyl compound is β-furyl lithium.

4. The process as claimed in claim 1 wherein said CD-trans-oid allylic alcohol has the structure

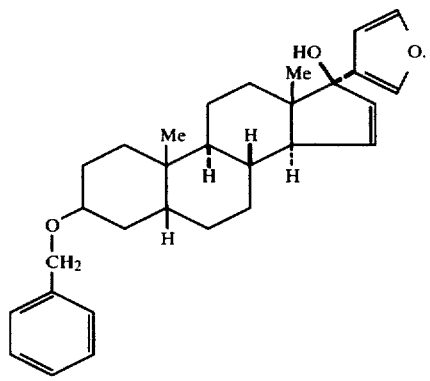

5. The process as claimed in claim 1 wherein said CD-trans-oid 15 β-hydroxyl compound has the structure

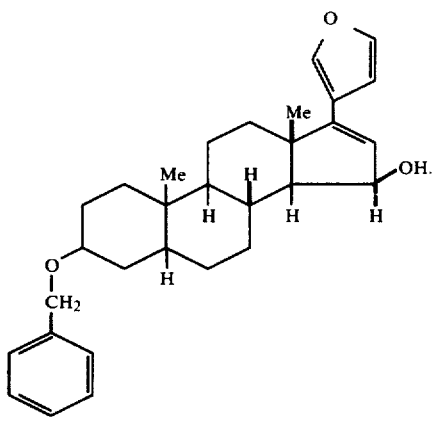

6. The process as claimed in claim 1 wherein said acetylation is effected by reacting CD-trans-oid allylic alcohol with acetic anhydride and pyridine.

7. The process as claimed in claim 1 wherein said allylic rearrangement is effected by refluxing the acetate produced by said acetylating step in aqueous acetone in the presence of calcium carbonate.

8. The process as claimed in claim 1 wherein said hydrogenating step is carried out in ethanol with 10% Pd/CaCO₃ at room temperature.

9. The process as claimed in claim 1 wherein said 17 β-furyl, 15 β-hydroxyl intermediate has the structure

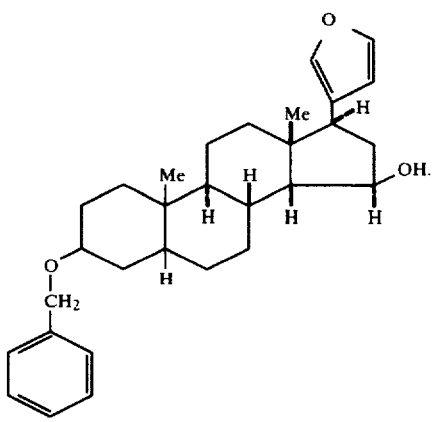

10. The process as claimed in claim 1 wherein said CD-trans-oid allylic alcohol initially has the hydroxyl group in the beta configuration and the furyl group in the alpha configuration and after said allylic rearrangement, said furyl group is then in the beta configuration.

11. A 17 B-furyl, 15B-hydroxyl intermediate has the structure

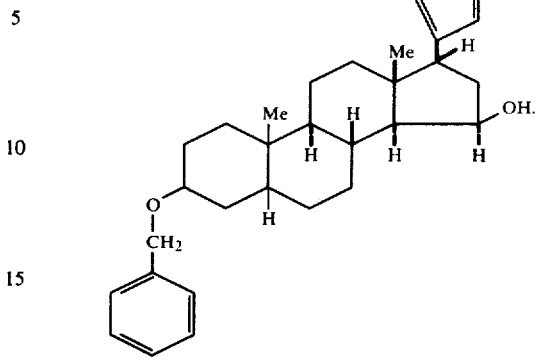

12. A process for the preparation of a cardenolide which comprises the steps of
(a) reacting an α,β unsaturated steroidal 17 ketone with an alkali or alkaline earth metal β-furyl compound to form a CD-trans-oid allylic alcohol;
(b) acetylating said alcohol and subjecting the resulting acetate to a stereospecific allylic rearrangement to produce a CD-trans-oid 15 β-hydroxyl compound;
(c) hydrogenating said 15 β-hydroxyl compound to form the 17 β-furyl, 15 β-hydroxyl intermediate and
(d) oxidizing said 17 β-furyl 16β-hydroxyl intermediates to produce said cardenolide.

13. The process as claimed in claim 12 wherein said oxidizing step is carried out utilizing a peracid.

14. The process claimed in claim 13 wherein said peracid is m-chloroperbenozic acid.

15. The process as claimed in claim 12 wherein said oxidizing step is carried out utilizing a reagent which generates a bromonium ion, wherein the isomer of said normal cardenolide is formed.

16. The process as claimed in claim 15 wherein said reagent is N-bromosuccinimide.

17. A process for the preparation of digitoxigenin which comprises the steps of
(a) reacting an α,β unsaturated steroidal 17 ketone having the structure

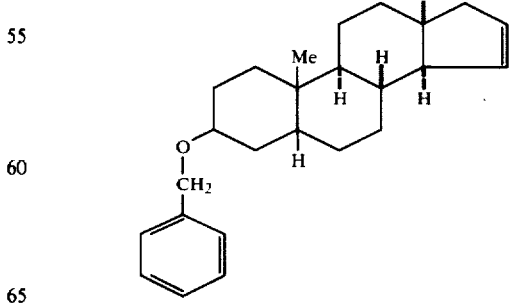

with β-furyl lithium to form a CD-trans-oid allylic alcohol having the structure

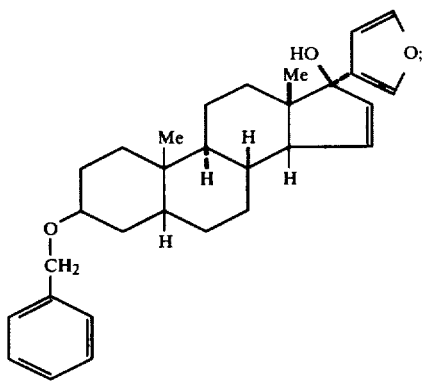

(b) acetylating said alcohol by reacting it with acetic anhydride and pyridine and subjecting the resulting acetate to a stereospecific allylic rearrangement by refluxing said acetate in aqueous acetone in the presence of calcium carbonate to produce a CD-trans-oid 15 β-hydroxyl compound having the structure

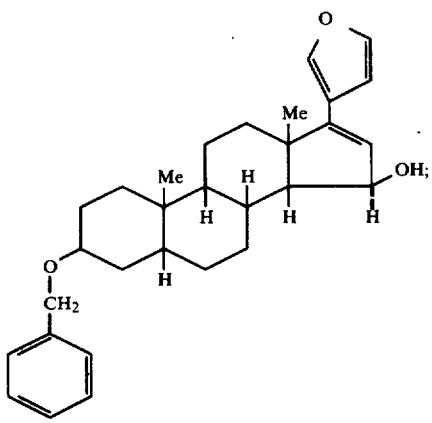

(c) hydrogenating said 15 β-hydroxyl compound by reaction in ethanol with 10% Pd/CaCO₃ at room temperature to produce a 17 β-furyl, 15 β-hydroxyl intermediate having the structure

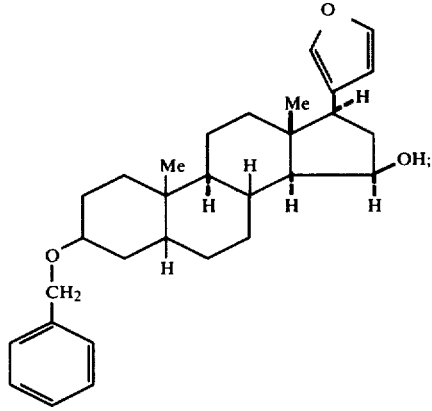

(d) oxidizing said 17 β-furyl, 15 β-hydroxyl intermediate by reaction with m-chloroperbenzoic acid to produce an hydroxylactone which is reacted with mesyl chloride to produce an unsaturated lactone having the structure

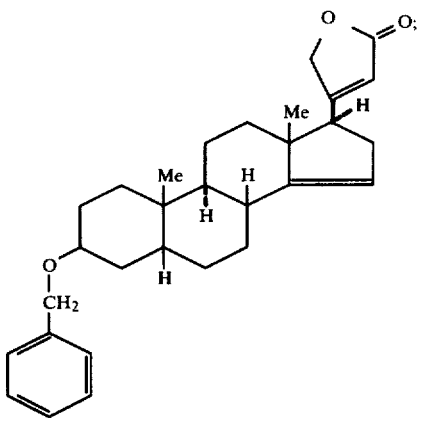

(e) reacting said lactone with N-bromoacetamide in an acetic acid-water-acetone mixture, reacting said reaction product with Ra-Ni in a mixture of methylene chloride, methanol and potassiumacetate to produce 3-benzyl digitoxigenin and then subjecting the benzyl group to hydrogenolysis over Pd-charcoal in an ethanol-benzene reaction to produce digitoxigenin.

18. A process for the preparation of digitoxigenin isomer which comprises the steps of
(a) reacting an α,β unsaturated steroidal 17 ketone having the struture

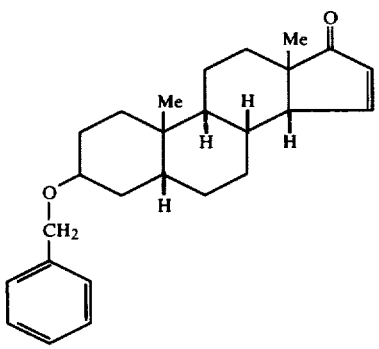

with β-furyl lithium to form a CD-trans-oid allylic alcohol having the structure

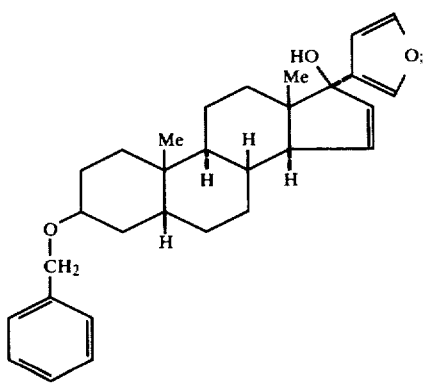

(b) acetylating said alcohol by reacting it with acetic anhydride and pyridine and subjecting the resulting acetate to a stereospecific allylic rearrangement by refluxing said acetate in aqueous acetone in the presence of calcium carbonate to produce a CD-trans-oid 15 β-hydroxyl compound compound having the structure

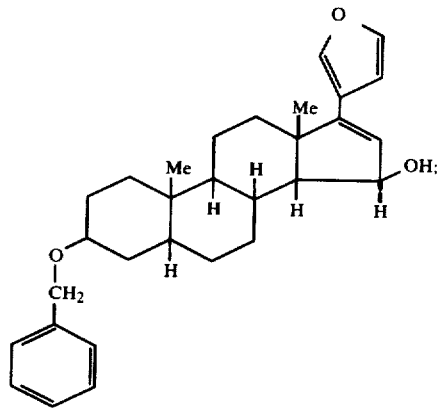

(c) hydrogenating said 15 β-hydroxyl compound by reaction in ethanol with 10% Pd/CaCO₃ at room temperature to produce a 17 β-furyl, 15 β-hydroxyl intermediate having the structure

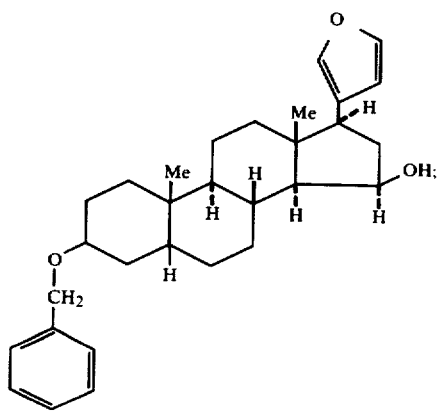

(d) oxidizing said 17 β-furyl, 15 β-hydroxyl intermediate with N-bromosuccinimide in a mixture of sodium acetate to produce a hydroxylactone which is reacted with mesyl chloride to produce an unsaturated lactone having the structure

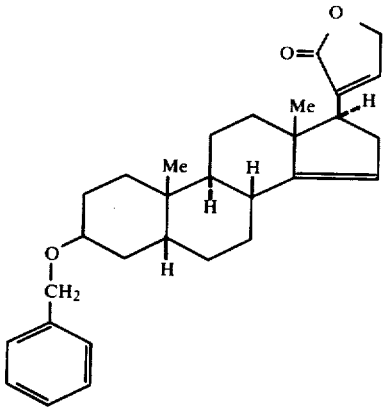

(e) reacting said lactone with N-bromacetamide in an acetic acid-water-acetone mixture, reacting said reaction product with Ra-Ni in a mixture of methylene chloride, methanol and potassium acetate to produce 3-benzyl digitoxigenin isomer having the structure

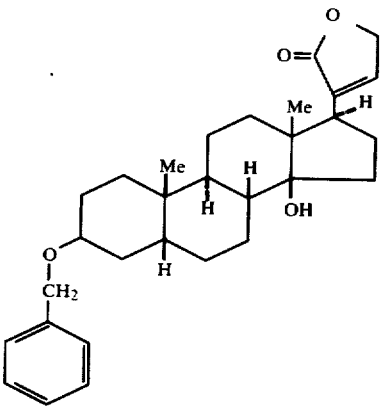

and then subjecting the benzyl group to hydrogenolysis over Pd-charcoal in an ethanol-benzene solution to produce digitoxigenin isomer having the structure

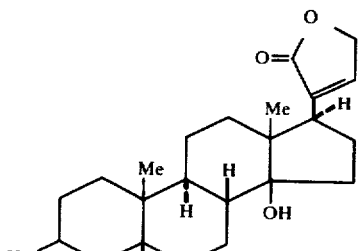

* * * * *